United States Patent
Couture et al.

(10) Patent No.: US 8,882,766 B2
(45) Date of Patent: Nov. 11, 2014

(54) METHOD AND SYSTEM FOR CONTROLLING DELIVERY OF ENERGY TO DIVIDE TISSUE

(75) Inventors: Gary M. Couture, Longmont, CO (US); Kristin D. Johnson, Louisville, CO (US); Robert Sharp, Boulder, CO (US); Jeff Unger, Superior, CO (US); Craig Weinberg, Denver, CO (US); Robert H. Wham, Boulder, CO (US)

(73) Assignee: Covidien AG (CH)

( * ) Notice: Subject to any disclaimer, the term of this patent is extended or adjusted under 35 U.S.C. 154(b) by 911 days.

(21) Appl. No.: 11/338,552

(22) Filed: Jan. 24, 2006

(65) Prior Publication Data

US 2007/0173811 A1    Jul. 26, 2007

(51) Int. Cl.
| | | |
|---|---|---|
| *A61B 18/14* | (2006.01) | |
| *A61B 18/12* | (2006.01) | |
| *A61B 17/00* | (2006.01) | |
| *A61B 18/00* | (2006.01) | |

(52) U.S. Cl.
CPC ... *A61B 18/1445* (2013.01); *A61B 2017/00154* (2013.01); *A61B 2018/00875* (2013.01); *A61B 2018/00702* (2013.01); *A61B 18/1206* (2013.01); *A61B 2018/00601* (2013.01); *A61B 18/1442* (2013.01)
USPC ............................................. 606/42; 606/37

(58) Field of Classification Search
CPC ........... A61B 18/1206; A61B 18/1442; A61B 18/1445; A61B 2018/00589; A61B 2018/00601; A61B 2018/00702; A61B 2018/00732; A61B 2018/00875

USPC ........................ 606/42, 45, 48–52, 34, 37, 41
See application file for complete search history.

(56) References Cited

U.S. PATENT DOCUMENTS

| | | | |
|---|---|---|---|
| 371,664 | A | 10/1887 | Brannan, et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler, et al. |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Int'l Search Report EP 05016399 dated Jan. 5, 2006.

(Continued)

*Primary Examiner* — Michael Peffley
*Assistant Examiner* — Samantha Good

(57) ABSTRACT

System and method for controlling delivery of energy to divide tissue are disclosed. The system comprises an electrosurgical instrument having an electrically energizable cutting element which communicates electrical energy to the tissue and a generator to supply the energy to the electrosurgical instrument which supplies the energy to the tissue in a first pulse to react the tissue, in slow pulses to create a desiccation line until impedance at the tissue has reached a threshold, and in rapid pulses to divide tissue across the desiccation line.

10 Claims, 6 Drawing Sheets

(56) References Cited

U.S. PATENT DOCUMENTS

| | | |
|---|---|---|
| 2,011,169 A | 8/1935 | Wappler |
| 2,031,682 A | 2/1936 | Wappler, et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs, et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,378,801 A * | 4/1983 | Oosten .................. 606/37 |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Heidmueller nee Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |

(56) References Cited

U.S. PATENT DOCUMENTS

| | | |
|---|---|---|
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |

(56) References Cited

U.S. PATENT DOCUMENTS

| | | |
|---|---|---|
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |

(56) References Cited

U.S. PATENT DOCUMENTS

| | | | |
|---|---|---|---|
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |

(56) References Cited

U.S. PATENT DOCUMENTS

| | | |
|---|---|---|
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078573 A1* | 4/2003 | Truckai et al. .................. 606/41 |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1* | 7/2003 | Goble et al. .................... 606/48 |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004567 A1* | 1/2005 | Daniel et al. .................... 606/50 |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |

(56) References Cited

U.S. PATENT DOCUMENTS

| | | |
|---|---|---|
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0222560 A1 | 10/2005 | Kimura et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |
| 2010/0305558 A1 | 12/2010 | Kimura et al. |

FOREIGN PATENT DOCUMENTS

| | | |
|---|---|---|
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |

(56) References Cited

FOREIGN PATENT DOCUMENTS

| | | |
|---|---|---|
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1 472 984 | 11/2004 |
| EP | 1472984 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001-029355 | 2/2001 |
| JP | 2001029356 A2 | 2/2001 |
| JP | 2001128990 A2 | 5/2001 |
| JP | 2005-253789 | 9/2005 |
| JP | 2006-501939 | 1/2006 |
| SU | 401367 | 11/1974 |
| WO | WO89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40881 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO02/080783 | 10/2002 |
| WO | WO 02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO02/080786 | 10/2002 |
| WO | WO 02/080786 | 10/2002 |
| WO | WO 02/080793 | 10/2002 |
| WO | WO02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO 02/080797 | 10/2002 |
| WO | WO02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06005185.1 dated Apr. 18, 2006.
Int'l Search Report EP 06008779.8 dated Jun. 13, 2006.

(56) References Cited

OTHER PUBLICATIONS

Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
International Search Report EP07001480.8 dated Apr. 12, 2007.
Int'l Search Report EP 04 752343.6 dated Jul. 20, 2007.
Int'l Search Report EP 06 024122.1 dated Mar. 19, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery"Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.

(56) References Cited

OTHER PUBLICATIONS

Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Official Action from corresponding Japanese Patent Application No. 2007-13173, mailed on Jan. 13, 2012, with English translation.
Australian First Examination Report dated Jan. 25, 2012 from counterpart Australian Application No. 2007200270 (2 pages).
Official Action mailed Jul. 27, 2013 from counterpart Japanese Application No. 2012-108450. (6 pgs.).

\* cited by examiner

METHOD AND SYSTEM FOR CONTROLLING DELIVERY OF ENERGY TO DIVIDE TISSUE

BACKGROUND

1. Technical Field

The present disclosure is directed to electrosurgical generators, and, more particularly, to a control system for electrosurgical generators used for tissue division procedures.

2. Background of Related Art

Electrosurgical generators are employed by surgeons in conjunction with electrosurgical instruments to perform a variety of surgical procedures including tissue division. An electrosurgical generator generates and modulates electrosurgical energy which is applied to the tissue by an electrosurgical instrument. Electrosurgical instruments may be either monopolar or bipolar and may be configured for open or endoscopic procedures.

In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated.

Bipolar electrosurgery is conventionally practiced using electrosurgical forceps-type device, where the active and return electrodes are housed within opposing forceps' jaws. The return electrode is placed in close proximity to the active (e.g., current supplying) electrode such that an electrical circuit is formed between the two electrodes (e.g., electrosurgical forceps). In this manner, the applied electrical current is limited to the body tissue positioned between the electrodes.

A need exists for a method and system for controlling energy output to divide tissue. Furthermore, a need exists for controlling energy in response to external input, including user input and/or input from sensors monitoring conditions, such as electrical and/or physical characteristics of the tissue.

SUMMARY

Disclosed are system and method for controlling delivery of energy to divide tissue. The system includes a generator for supplying electrical energy to an electrosurgical instrument. The electrosurgical instrument includes an electrically energizable cutting element which communicates the energy to the tissue to divide it. Energy is applied in several stages, during the first state a first pulse of energy is supplied to react the tissue. In the second stage, energy is supplied in "slow" pulses until an impedance threshold is reached to create a desiccation line in the tissue. In the third stated, energy is supplied in "rapid" pulses to divide the tissue along the desiccation line. The division is terminated upon identifying complete separation of the tissue. During the division process, impedance and temperature of the tissue as well as voltage and current phase, and power levels are measured. If the obtained measurements exceed a predetermined threshold the division process is complete and the energy supply is terminated.

According to one embodiment of the present disclosure, a system for controlling delivery of energy to divide tissue is disclosed. The system includes an electrosurgical instrument having an electrically energizable cutting element which communicates energy to the tissue and a generator to supply the energy to the electrosurgical instrument which supplies the energy to the tissue in a first pulse to react the tissue, in slow pulses to create a desiccation line until impedance at the tissue has reached a threshold, and in rapid pulses to divide tissue across the desiccation line.

According to another embodiment of the present disclosure, a method for controlling delivery of energy to divide tissue is disclosed. The method includes the step supplying energy to an electrosurgical instrument having an electrically energizable cutting element which communicates the energy to the tissue from a generator. The method also includes the steps of communicating the energy to the tissue in a first pulse to react the tissue, slow pulsing the energy to create a desiccation line until impedance at the tissue has reached a threshold, and rapid pulsing the energy to divide tissue across the desiccation line.

According to a further embodiment of the present disclosure, a method for regulating application of electrosurgical energy for performing tissue division is disclosed. The method includes the steps of applying a first electrosurgical energy waveform to condition the tissue, determining whether the tissue has been conditioned, and applying a second electrosurgical energy waveform to divide the conditioned tissue.

According to a final embodiment of the present disclosure, a system for regulating application of electrosurgical energy for performing tissue division is disclosed. The system includes a generator configured to apply a first electrosurgical energy waveform to condition the tissue, the generator including a control module for determining whether the tissue has been conditioned, the generator further configured to apply a second electrosurgical energy waveform to divide the conditioned tissue.

BRIEF DESCRIPTION OF THE DRAWINGS

Various embodiments will be described herein below with reference to the drawings wherein.

DETAILED DESCRIPTION

Figure 1:
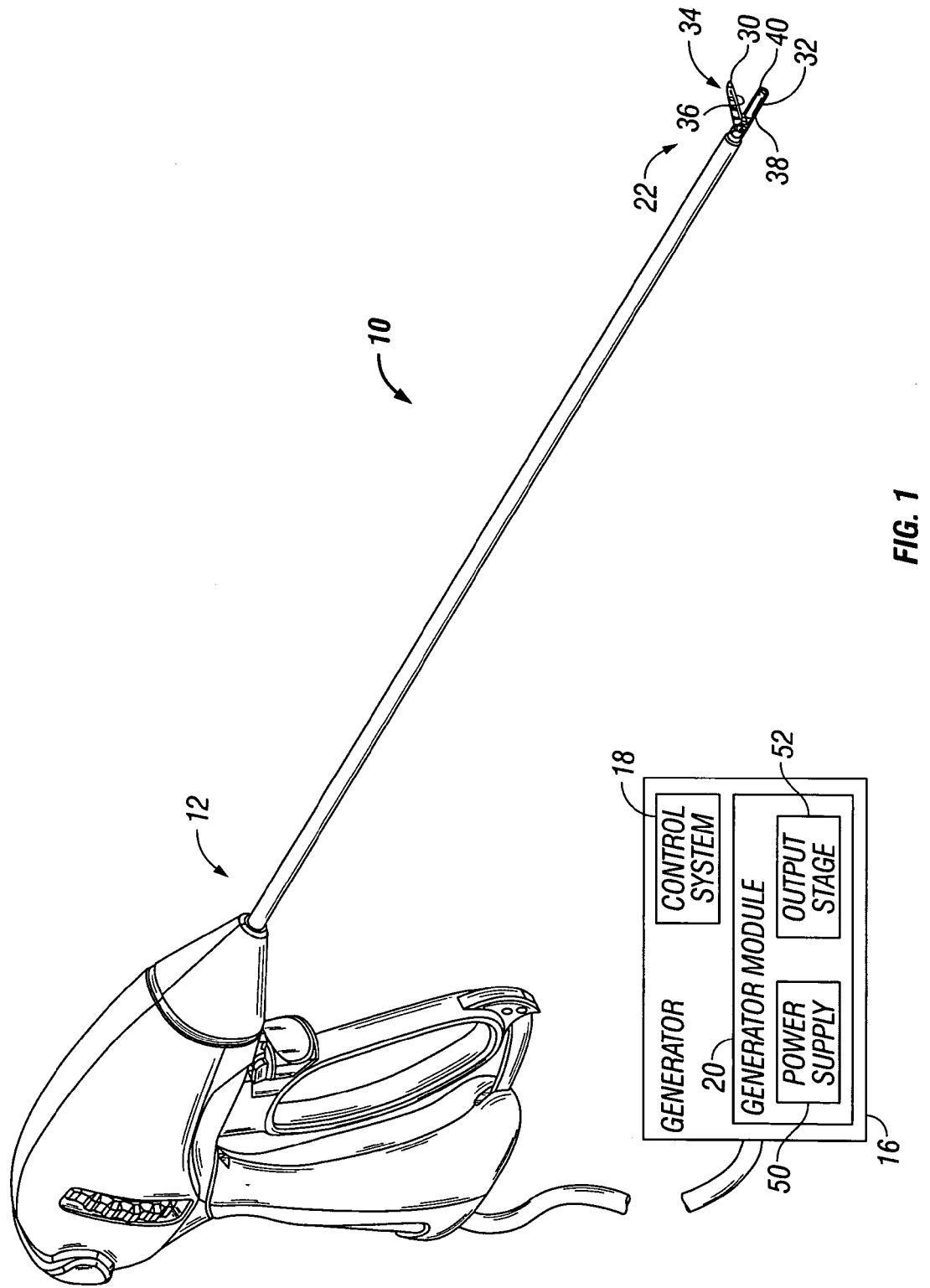
FIG. 1 is a perspective view of an exemplary electrosurgical system including an endoscopic forceps configured for electrical division of tissue in accordance with the present disclosure.

Reference should be made to the drawings where like reference numerals refer to similar elements throughout the various figures. Preferred embodiments of the present disclosure will be described herein below with reference to the accompanying drawings. In the following description, well-known functions or constructions are not described in detail to avoid obscuring the present disclosure in unnecessary detail.

Tissue cutting or tissue division occurs when heating of the tissue leads to expansion of intracellular and/or extra-cellular fluid, which may be accompanied by cellular vaporization, desiccation, fragmentation, collapse and/or shrinkage along a desiccation line in the tissue. By focusing the electrosurgical energy and heating along the desiccation line, the cellular reactions are localized creating a fissure. Localization and maximization of the cutting effect is achieved by utilizing one or more of various geometrical electrode and insulator configurations and regulating the electrosurgical energy delivered to the tissue. Further, the tissue condition may be regulated and energy delivery controlled by utilizing a generator and feedback algorithm.

For the purposes herein, the term "cut effect" or "cutting effect" refers to the actual division of tissue by one or more of the electrical or electromechanical methods or mechanisms described below. The term "cutting zone" or "cut zone" refers to the region of tissue where tissue cutting will take place. The term "cutting process" refers to steps that are implemented before, during and/or after tissue division that tend to influence the tissue as part of achieving the cut effect.

FIG. 1 shows a schematic diagram of one embodiment of the presently-disclosed electrosurgical system 10 having an endoscopic electrosurgical instrument 12 for delivering electrosurgical energy to a patient at a surgical site for cutting or dividing tissue. An electrosurgical generator 16 is also provided having a generator module 20 for generating electrosurgical energy and a control system 18 for controlling the generator module 20, which modulates the electrosurgical energy output. The modulated electrosurgical energy is thereafter provided by the generator 16 to the electrosurgical instrument 12.

The electrosurgical instrument 12 is an endoscopic forceps instrument which includes an end-effector assembly 22 having appropriate structures for affecting tissue, such as grasping, dissecting and/or clamping tissue. Those skilled in the art will appreciate that the cutting process discussed herein below may also be applied to an open electrosurgical instrument. The end-effector assembly 22 includes jaw members 30, 32 and at least one delivery device for communicating electrosurgical energy to the tissue, such as an electrode assembly 34 having at least one electrode for delivering the electrosurgical energy to the patient. It is envisioned that mechanical action, such as clamping, may also be used by the electrosurgical instrument 12 in addition to the application of electrosurgical energy to obtain a surgical effect. As can be appreciated, the electrode assembly 34 may be configured as monopolar, bipolar or macro-bipolar. Further, the electrosurgical instrument may be configured as suitable for performing endoscopic or open surgery.

The jaw members 30 and 32 each include a tissue contacting surface 36 and 38, respectively, which cooperate together to engage the tissue during cutting. At least one of the jaw members, e.g., jaw member 32, includes at least one electrically energizable cutting element 40 disposed therein, wherein the cutting element 40 is part of the electrode assembly 34. The cutting element(s) 40 may further include additional electrodes for other surgical procedures, such as a combination of sealing electrodes, which may be provided as electrically conductive surfaces at the tissue contacting surfaces 36 and 38. Insulators may be provided for providing insulation between conductive elements. The cutting element(s) 40 may be electrically conductive, non-conductive, made from an insulative material with a conductive coating disposed thereon or a combination thereof. An electrosurgical instrument for cutting and sealing tissue is described in U.S. Pat. No. 5,702,390. Electrical cutting of tissue is described in U.S. patent application Ser. No. 10/932,612, entitled VESSEL SEALING INSTRUMENT WITH ELECTRICAL CUTTING MECHANISM, by Johnson, filed on Sep. 2, 2004, the contents of which are herein incorporated by reference in their entirety.

The electrode assembly 34 may utilize various geometrical configurations of electrodes, cutting element(s) 40, insulators, partially conductive materials and semiconductors to produce or enhance the cutting effect. For example, the geometrical configuration of the electrodes and insulators may be configured to produce a so-called "cut effect" which may be directly related to the amount of vaporization or fragmentation at a point in the tissue or the power density, temperature density and/or mechanical stress applied to a point in the tissue. Moreover, it is envisioned that the geometrical configurations of the electrodes and insulators may be designed such that they act like electrical sinks or insulators to influence the heat effect within and around the tissue during the sealing or cutting processes.

The particular geometrical configuration of the cutting element(s) 40, tissue contacting surface 36 and 38 and insulators is designed to focus current into high areas of power density to produce a cutting effect and/or reduce the likelihood of current straying to adjacent tissue which may ultimately damage the adjacent tissue structures. A variety of polarity configurations of the cutting element(s) 40 and tissue contacting surface 36 and 38 can be utilized to enhance or facilitate cutting. Additionally, surface areas of electrodes having different poles may be configured for establishing selected surface area ratios between the electrical poles for focusing electrical energy at the tissue. The power density and/or current concentration is further affected by proximity of the cutting element(s) 40 to the return electrode(s), e.g., tissue contacting surfaces 36 and/or 38. Furthermore, opposite jaw members may be configured as mirror images or may include a different geometrical configuration or be made of different materials.

The electrosurgical instrument 12 may be configured for performing a variety of electrosurgical procedures in addition to cutting, such as tissue sealing or coagulating. Accordingly, the cutting element(s) 40 may be substantially dull so that the surgeon is free to manipulate, grasp and clamp the tissue for performing other surgical or electrosurgical procedures with the electrosurgical instrument 12 without the cutting element(s) 40 mechanically cutting into the tissue. The dull cutting element(s) 40 may provide a uniform gap between sealing surfaces 36, 38 during a procedure other than cutting, such as during a sealing phase, and prevent the electrode assembly 34 from shorting during an electrosurgical procedure, such as during sealing and cutting phases. In this fashion, the tissue is initially sealed and thereafter cut without the need to re-grasp the tissue.

The electrosurgical generator 16 generates electrosurgical energy, which may be RF (radio frequency), microwave, ultrasound, infrared, ultraviolet, laser, thermal energy or other electrosurgical energy. The exemplary electrosurgical module 20 shown in FIG. 1 generates RF energy and includes a power supply 50 for generating energy and an output stage 52 which modulates the energy which is provided to the delivery device(s), such as the electrode assembly 34, for delivery of the modulated energy to a patient. In one embodiment, the power supply 50 is a high voltage DC or AC power supply for producing electrosurgical current, where control signals generated by the control system 18 adjust parameters of the voltage and current output, such as magnitude and frequency. The output stage 52 modulates the output energy, such as via a waveform generator based on signals generated by the control system 18 to adjust waveform parameters, e.g., waveform shape, pulse width, duty cycle, crest factor, and/or repetition rate. The control system 18 is coupled to the generator module 20 by connections that may include wired and/or wireless connections for providing the control signals to the generator module 20. The control system 18 may be a closed loop or open loop control system.

It is also contemplated that the generator 16 may be connected remotely, e.g., via a network, such as the internet, to an off-site server and/or database providing information, such as instrument operating information, mappings, algorithms and/or programs. Updated information may be provided on a regular basis and downloaded to the generator as needed and/or prior to surgery. As can be appreciated, this enables the user to obtain updated information regarding operation of the instrument, electrical parameters, and ideal curves for optimizing an electrosurgical cutting procedure. In addition, this also enables the generator manufacturer to provide updated information on a regular basis. It is also contemplated that the user may be able to receive diagnostics remotely in this fashion relating to the instruments and/or generators being utilized, either on demand by the user, prior to an operation or automatically during a scheduled download.

Preferably, the generator 16 delivers energy to the tissue in a variety of waveforms, including continual, pulsed, spiked and/or a ramped. Pulsing refers to a variation of output for a specified duration. Several pairs of pulses having a "high" and a "low" pulse could be provided in a series. The duration of the "high" and "low" pulses may vary within a pair or from pair to pair. The "high" pulse typically refers to a state of higher power delivery and the "low" pulse typically refers to a state of lower power delivery. Spiking refers to a high level of energy applied over a brief period of time. An energy ramp refers to increasing or decreasing levels of energy.

It has also been determined that RF pulsing may be used to more effectively cut tissue during particular phases of the cutting process. For example, if the energy is not pulsed during an early phase of the procedure, the tissue may not initially cut, but may desiccate, since tissue impedance remains high during the initial stages of cutting. By providing the energy in short, high energy pulses, it has been found that the tissue is more likely to cut. Moreover, a feedback loop of signals generated by sensors sensing tissue properties (e.g., tissue temperature, tissue impedance, current through the tissue) can be provided for automatically adjusting parameters of the energy, such as intensity and number of pulses, for maximizing the cutting effect and reducing unwanted tissue-effects, such as charring and thermal spread. An exampled of an electrosurgical system having a generator controlled by an impedance sensor is shown and described in commonly-owned U.S. Pat. No. 6,203,541 entitled "Automatic Activation of Electrosurgical Generator Bipolar Output" which is hereby incorporated by reference herein in its entirety.

Figure 2:
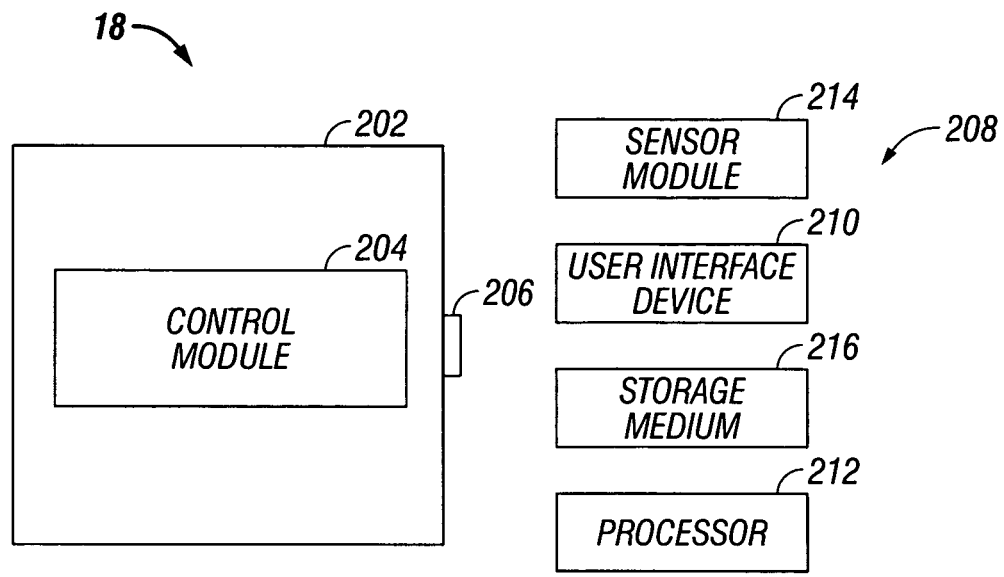
FIG. 2 is a block diagram of a control system of the electrosurgical system shown in FIG. 1.

With reference to FIG. 2, the control system 18 is shown, including a processor 202 having a control module 204 executable on the processor 202, and one or more input/output (I/O) ports 206 for communicating with one or more peripheral devices 208 (wherein "peripheral" is used in this case as peripheral to the at least one processor 202 and/or the electrosurgical instrument 12). The peripheral device 208 is in wired or wireless communication with the processor 202 and includes a user interface device 210, a peripheral processor 212, a sensor module 214, and a storage medium 216. It is envisioned that the components of the peripheral device 208 and functions performed therein may be incorporated within the generator 16.

The control module 204 processes information and/or signals input to the processor 202 by the peripheral device(s) 208 and generates control signals for modulating the electrosurgical energy in accordance with the input information and/or signals. Information input via the peripheral device 208 may include pre-surgical data entered prior to the electrosurgical procedure or information entered and/or obtained during the electrosurgical procedure through the sensor module 214. The information may include requests, instructions, ideal mapping(s) (e.g., look-up-tables, continuous mappings, etc.), sensed information and/or mode selection.

The control module 204 regulates the generator 16, e.g., the power supply 50 and/or the output stage 52, which adjust various parameters of the electrosurgical energy delivered to the patient during the electrosurgical procedure. Parameters of the delivered electrosurgical energy which may be regulated include, for example, voltage, current, resistance, intensity, power, frequency, amplitude, and/or waveform parameters, e.g., waveform shape, pulse width, duty cycle, crest factor, and/or repetition rate of the output and/or effective energy.

The control module 204 preferably includes software instructions executable by the processor 202 for processing algorithms and/or data received by the peripheral device(s) 208, and for outputting control signals to the generator module 20. The software instructions may be stored in a storage medium such as a memory internal to the processor 202 and/or a memory accessible by the processor 202, such as an external memory, e.g., an external hard drive, floppy diskette, CD-ROM, etc.

Control signals from the control module 204 for controlling the generator 16 may be converted to analog signals by a digital-to-analog converter (DAC) which may be included in the processor 202 or be external thereto. It is contemplated that the processor 202 may include circuitry, e.g., analog devices, for processing information input by the peripheral device(s) 208 and determining the control signals to be provided to the generator 16. Further, an audio or visual feedback monitor or indicator (not shown) may be employed to convey information to the surgeon regarding the status of a component of the electrosurgical system or the electrosurgical procedure.

Control signals provided to the generator module 20 are determined by processing (e.g., performing algorithms), which may include using information and/or signals entered by the peripheral device(s) 208. Furthermore, the control signals may be determined by accessing further information and/or desired values, such as by accessing a data base and/or consulting a mapping (e.g., an ideal curve, look-up-table, etc.) stored by or accessible by the control module 204.

The control module 204 preferably automatically recognizes various phases of a cutting procedure, where the cutting procedure may include a number of phases, such as (a) at least one phase preceding the cutting process (e.g., before cutting begins, which may include a sealing and/or cauterizing phase); (b) at least one phase during the cutting process, such as a fragmenting phase, a melting phase and/or a tissue rehydration phase; and/or (c) at least one phase following the cutting process, such as division recognition and fragmentation clean-up. Recognition of the completion of a phase or commencement of a new phase may be in accordance with sensed information, such as from sensors of the sensor module 214 sensing tissue responses, and/or timing information. Phase status information may also be input by an operator.

The control module 204 controls the output of the generator 16 so that the energy is suitable for dividing tissue, including localizing or focusing electrosurgical energy in the cut zone during the cutting process while minimizing energy effects to surrounding tissue; focusing the power density in the cut zone during the cutting process; creating an area of increased temperature in the cut zone during the cutting process (e.g., heating that occurs within the tissue or heating the tissue directly with a heat source); minimizing tissue volume in or around the cut zone to create more favorable conditions for tissue cutting; controlling energy and power delivery to allow vaporization to enhance and or contribute to the cutting process, e.g., controlling the energy delivery to vaporize both intracellular and/or extracellular fluids and/or other cellular materials and foreign fluids within the cut zone; fragmenting the tissue or cellular material during the cutting process to enhance tissue division in the cut zone; melting or collapsing the tissue or cellular material during the cutting process to enhance tissue division in the cut zone, e.g., melting the tissue to create internal stress within the tissue to induce tissue tearing; and controlling tissue temperature, arcing, power density and/or current density during the cutting process to enhance tissue division in the cut zone.

Methods for achieving the control described above include pulsing the energy delivery to influence the tissue in or around the cut zone; spiking the energy delivery (e.g., creating a momentary condition of high energy application for a brief period of time) with an intent to influence the tissue in or around the cut zone during the cut process; applying increasing or decreasing energy (e.g., an energy ramp) by varying the energy output level to control a tissue response; conditioning the tissue before, during and/or after the cutting process to create more favorable tissue conditions for cutting; making decisions regarding when and how to proceed with an algorithm for controlling energy delivery based on tissue condition feedback; making decisions regarding when and how to proceed with an algorithm for controlling energy delivery based on a predetermined time constant; and/or applying a constant amount of energy over a given time interval or until a tissue condition is achieved.

Conditioning the tissue may include, for example, a tissue pre-heating phase before the cutting process and a tissue rehydration phase during the cutting process. Determining the current phase of the cutting procedure may include determining from tissue response feedback if a desired state has been achieved.

In addition, the control module 204 may further control application of various mechanical elements to the tissue, such as pressure, tension and/or stress (either internally or externally) to enhance the cutting process; and delivering and controlling various other tissue treatments before or during the cutting process to enhance tissue cutting, e.g., tissue sealing, cauterization and/or coagulation. For example, the electrode assembly 34 may be controlled for independently activating cutting element(s) 40 and/or conductive sealing surfaces 36, 38, or independently controlling parameters of energy output therefrom, respectively, in response to user requests or automatically, such as in accordance with an algorithm or sensed feedback (e.g., upon sensing that a sealing or cutting phase is complete). In an exemplary cutting procedure, the cutting element(s) 40 is energized with a first electrical potential "+" and the opposing sealing surfaces 36 and 38, or selected portions thereof are energized with a second electrical potential "−".

The control module 204 regulates the electrosurgical energy in response to feedback information, e.g., information related to tissue condition at or proximate the surgical site. Processing of the feedback information may include determining: changes in the feedback information; rate of change of the feedback information; and/or relativity of the feedback information to corresponding values sensed prior to starting the procedure (pre-surgical values) in accordance with the mode, control variable(s) and ideal curve(s) selected. The control module 204 then sends control signals to the generator module 20 such as for regulating the power supply 50 and/or the output stage 52. It is contemplated that the operator may enter requests via the user interface 210 that override the control information provided by the control module 204.

Regulation of certain parameters of the electrosurgical energy or a tissue response may include recognition of an event, such as a lapse of a period of time or recognition of a rise, fall, leveling, achievement of a target value, achievement of a target change, achievement of a target rate of change and/or achievement of a target change of rate of change of a sensed property (e.g., impedance at the cutting site). Recognition of the event is used for determining what phase of a procedure or stage of a selected ideal mapping has been reached for driving the property along the ideal mapping. It is envisioned that other methods that are known in the art may be used by the control module 204 to control the generator 16 and regulate the electrosurgical energy.

The user interface device 210 may include a switch to allow the surgeon to selectively activate one or more tissue contacting surfaces 36, 38 or the cutting element 40 independently of one another. As can be appreciated, this may allow the surgeon to initially seal tissue and then activate the cutting element by simply turning the switch. It is also envisioned that the sensor module 214 includes a smart sensor assembly (e.g., a smart sensor, smart circuit, computer, and/or feedback loop, etc.) which may cooperate with the switch for automatically triggering the switch to change between a "sealing" mode and a "cutting" mode upon the satisfaction of a particular condition. For example, the smart sensor may include a feedback loop which indicates when a tissue seal is complete based upon one or more of the following parameters: tissue temperature, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal. Advantageously, the surgeon does not necessarily need to re-grasp the tissue to cut, since the cutting element is already positioned proximate the ideal, center cutting line of the seal.

The sensor module 214 senses various electrical and/or physical parameters or properties at the operating site and communicates with the control module 204 to regulate the output electrosurgical energy. It is envisioned that the sensor module 214 may be configured to measure, i.e., "sense", various electrical, physical and/or electromechanical conditions, such as at or proximate the operating site, including: tissue impedance, tissue temperature, leakage current, applied voltage, applied current, tissue thickness, volume of tissue between jaws of electrosurgical instrument, tissue light transmission, reflectivity and/or absorption properties, tissue moisture content, tissue elastomeric properties, tissue viability, indications of imminent or actual damage to tissue surrounding the surgical site, and/or tissue reactive pressure. For example, sensors of the sensor module 214 may include optical sensor(s), proximity sensor(s), pressure sensor(s), tissue moisture sensor(s), temperature sensor(s), and/or real-time and RMS current and voltage sensing systems. Preferably, the sensor module 214 measures one or more of these conditions continuously or in real-time such that the control module 204 can continually modulate the electrosurgical output in real-time. In the case where analog signals corresponding to the sensing are provided by the sensor module 214, the analog signals are converted to digital signals via an analog-to-digital converter, which in turn are provided to the control module 204.

It is further envisioned that more than one sensor of the sensor module for sensing a particular property may be provided at different positions, such as along a jaw member of the electrosurgical instrument. For example, proximity sensors positioned at several different positions along the jaw member may sense varying tissue thickness along the jaw member.

Sampling may be employed by the sensor module 214 for sensing properties. Signals corresponding to sensing by the sensor module 214 may be sampled, such as during the process of converting the signals to digital, and/or by the control module for regulating the generator 16 in accordance with the sampled signals.

The at least one storage medium 216 may store instrument operating information, diagnostic information, ideal mappings for optimizing parameters at particular phases of a procedure, algorithms or programs which can be updated and provided (e.g., accessible by or downloaded to) to the generator and/or control module 204 as needed and/or prior to surgery.

A method for controlling an electrosurgical generator in accordance with the present disclosure will be described in relation to FIGS. 3 and 4. At step 402, the control module 204 processes any pre-surgical data entered. At step 404, the electrosurgical instrument 12 interfaces with tissue by grasping the tissue between The jaw members 30 and 32 and the control module 204 controls the generator 16 and regulates energy output for phase I of the electrosurgical procedure, where phase I is indicated by reference numeral 302 in FIG. 3. Phase I is initiated with the onset of RF energy as the electrosurgical instrument 12 interfaces with the tissue. Purpose of phase I is to supply energy to heat the tissue held between the jaw members 30 and 32 to a point where the impedance of the tissue rises to a specified level, ranging from about 1 Ohm to about 200 Ohms above the minimum value reached, and/or the point of vaporization of tissue fluids. After that point is reached (e.g., end of phase I), energy supply is halted. It is also envisioned that at the end of phase I that the supply of energy is decreased sufficiently to minimize energy delivery and heating without completely shutting off the energy supply, so that some electrical energy supplied is sufficient to accurately measure the tissue state through feedback sensors.

It is further envisioned that in certain situations phase I may be shortened or omitted. More specifically, in situations where tissue has been pre-treated through another process that places tissue into state of fusion and/or sealing or where tissue has been heated, etc.

At step 406, a determination is made if a predetermined condition has been achieved, such as a desired reaction, e.g., when a first predetermined tissue condition has been sensed. If the first predetermined condition has not been achieved, the control module 204 continues to control the generator for phase I application of the electrosurgical energy. The control module 204 may regulate, for example, the voltage, current and/or power of the output electrosurgical energy. The tissue conditioning prepares the tissue for optimal effect during the next phase(s) of the electrosurgical procedure. At the end of phase I, intra- and inter-cellular fluids have begun to vaporize in the cut region. However, by halting or significantly decreasing the energy as to no longer affect the tissue after the point of reaction, adjacent tissue to the cut region has maintained hydration and vaporization has been kept to a minimum.

At the end of phase I, if division has occurred and/or the tissue has been sufficiently broken down as to allow for division with minimal physical force, the electrosurgical energy supply is shut down and the division process is completed. If division has not occurred during phase I, the energy delivery process enters phase II, the purpose of which is to focus energy delivery into a local region, breaking down the tissue in the cut zone, which initiates and/or finalizes division.

Figure 3:
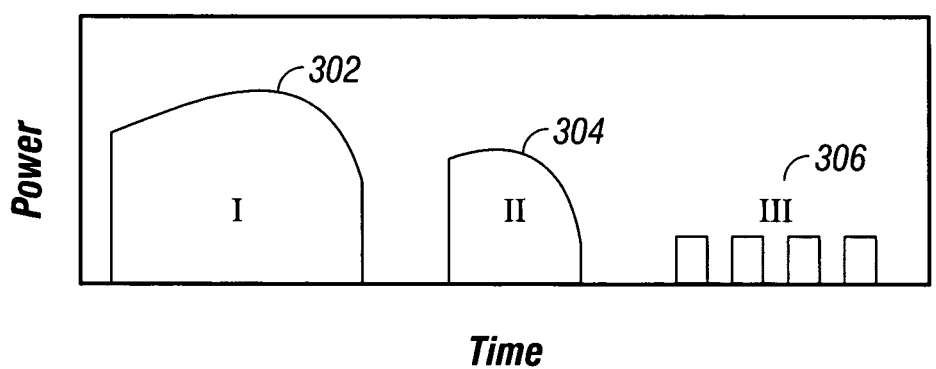
FIG. 3 is a graph of power versus time for energy applied during an electrosurgical procedure in accordance with the present disclosure.
Figure 4:
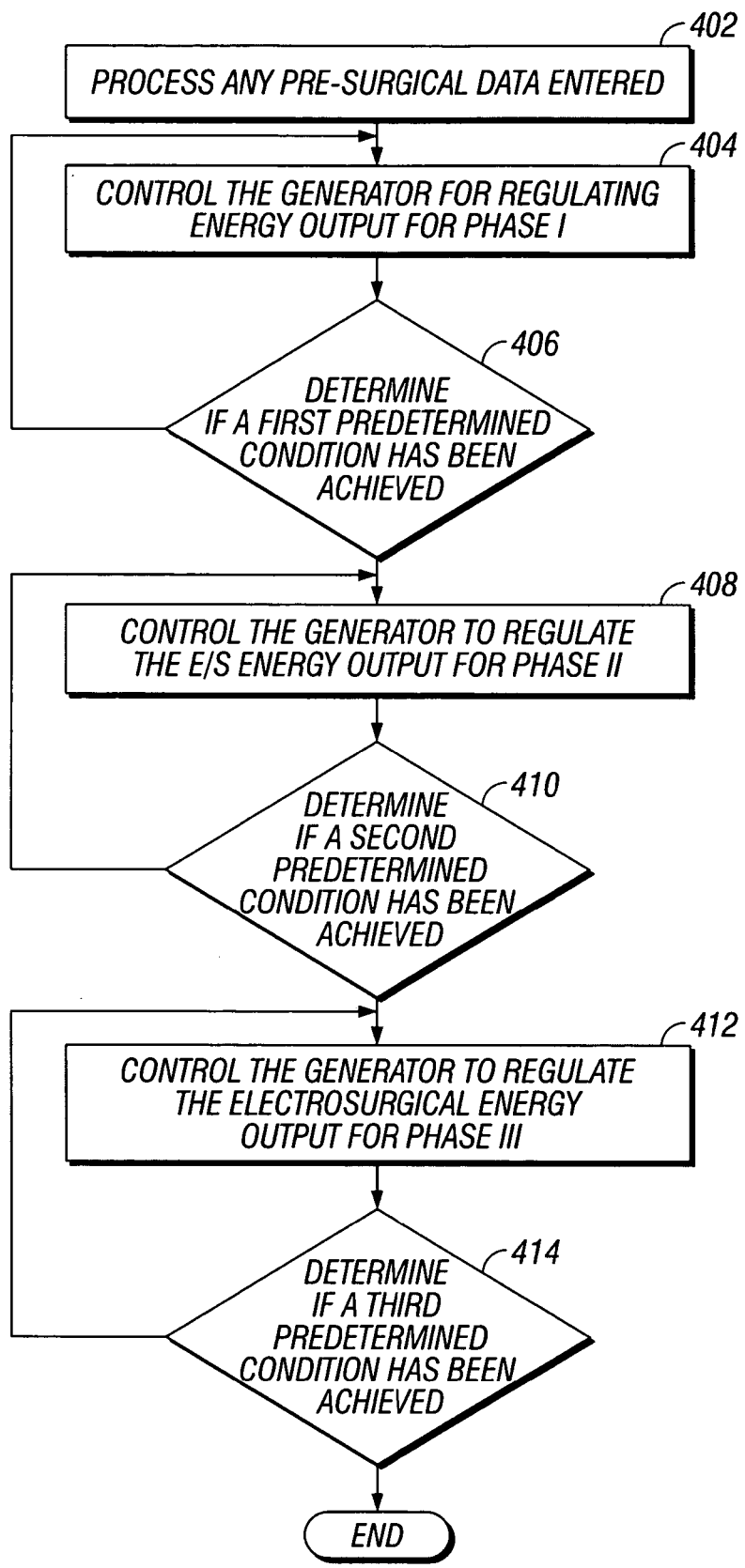
FIG. 4 is a flowchart illustrating a method for regulating application of electrosurgical energy during a procedure in accordance with the present disclosure.

After it is determined that the first predetermined condition has been achieved, step 408 is executed, in which the control module 204 proceeds to control the generator 16 to regulate the electrosurgical energy output for phase II of the electrosurgical procedure, where phase II is indicated by reference numeral 304 in FIG. 3. The preferred energy delivery modality during phase II is a pulsed series, consisting of an on-pulse and off-pulse periods, since through pulsing, sufficient energy can be supplied to the tissue to promote degradation thereof and fluid vaporization. The degradation and other associated changes of the tissue can be kept isolated to a small localized region, defining the cut zone. Therefore, through pulsing, the state of the tissue adjacent to the cut zone is kept hydrated. Hydration maintains low impedance at the tissue which permits transfer of maximum energy through the tissue during the energy pulses and focusing of the energy into the affected cut zone. Additionally, during the energy pulsing, the tissue in the cut zone is broken down to a point of fragmentation.

It is also envisioned that energy delivery during phase II can be of non-pulsing or other modalities which allow energy delivery to be focused within the cut zone of the tissue. One example of a non-pulsing modality may include delivery directed based upon real-time or predetermined interval values, such as tissue property values (e.g., impedance, current, temperature, etc.) Therefore, a derivative or integral calculation of the values occurring in real-time or following a predetermined path may be used to direct the energy levels over time in a non-pulsing modality during phase II to focus energy into the cut zone.

At step 410, a determination is made if a second predetermined condition has been achieved from available feedback, which is based on impedance. It is envisioned that other feedback can be utilized to identify a second predetermined condition such as current, voltage, temperature, etc. Feedback is collected while energy is supplied to the tissue through continuous monitoring of tissue impedance for a specific rise thereof and/or absolute value and/or relative value and/or minimum impedance value before the off-pulse period. For the on and off pulses during phase II, values and ranges have nearly infinite possibilities ranging from constant levels to non-linear combinations of previous information, specific to tissue types and directly related to the power levels. It is envisioned that on-pulse stage can be controlled in a plurality of ways, such as, allowing the period to continue for a set period of time, monitoring current, voltage, power, temperature, etc. until a predetermined threshold is reached. The duration of the off-pulse period is determined in a plurality of ways, such as, allowing the period to continue for a set period of time, monitoring current, voltage, power, temperature, etc. until a predetermined threshold is reached. The purpose of both of the on-pulse and off-pulse monitoring is to verify that the tissue is at an appropriate level to allow for repeated energy delivery to the cut zone.

Phase II continues until the second predetermined condition is satisfied, which may be a time related event and/or an event related to feedback information, e.g., sensed impedance across tissue, and/or current, voltage and/or power measured at the surgical site. The second predetermined condition and/ or the parameters of the applied electrosurgical energy may be determined in accordance with information gathered during phase I and/or phase II of the electrosurgical procedure.

At the end of the phase II, if division has occurred and/or the tissue has been sufficiently broken down as to allow for division with minimal physical force, the electrosurgical energy supply is shut down and the division process is completed. If division has not occurred during phase II, the energy delivery process enters phase III.

If the second predetermined condition has not been achieved, the control module 204 continues to control the generator for phase II application of the electrosurgical energy. The control module 204 continues to regulate, for example, the voltage, current and/or power of the output electrosurgical energy.

It is also envisioned that phase II may include application of electrosurgical energy in the form of a continual waveform or a waveform having pulses, spikes and/or a ramp. Amplitude of the waveform may vary or remain constant.

When it is determined that the second predetermined condition has been achieved, step 412 is executed, in which the control module 204 proceeds to control the generator 16 to regulate the electrosurgical energy output for phase III of the electrosurgical procedure, where phase III is indicated by reference numeral 306 in FIG. 3.

Phase III includes a series of rapid pulses defined by "quick" on and off pulses. The rapid pulse train serves to "fatigue" the tissue, promoting fragmentation and continually vaporizes any remaining tissue fluid. Control of the phase III pulsing is based on predetermined duration of on and off period, monitoring of the current, voltage, power, impedance, etc. for predetermined levels. In addition to predetermined durations, it is envisioned that these rapid pulses be based on real-time feedback from the tissue through either the impedance, current, voltage, temperature, etc.

An additional modality for energy delivery during phase III includes constant energy delivery at levels determined through feedback. Energy delivery ceases after division has completed or the tissue is effectively broken down so that division can be accomplished with minimal force.

At step 414, a determination is made if a third predetermined condition has been achieved. If the third predetermined condition has not been achieved, the control module 204 continues to control the generator for phase III application of the electrosurgical energy. The control module 204 may regulate, for example, the voltage, current and/or power of the output electrosurgical energy. Phase III may include application of electrosurgical energy in the form of a continual waveform or a waveform having pulses, spikes and/or a ramp. Amplitude of the waveform may vary or remain constant. During phase III the energy application is configured for creating a final or a complete tissue division. At the end of phase III, the tissue is completely divided or broken down to such an extent that division is achieved with minimal application of force.

The third predetermined condition may be a time related event and/or an event related to feedback information, e.g., sensed impedance across tissue, and/or current, voltage and/or power measured at the surgical site. The third predetermined condition and/or the parameters of the applied electrosurgical energy may be determined in accordance with information gathered during phase I, II and/or III of the electrosurgical procedure.

When it is determined that the third predetermined condition has been achieved, the electrosurgical procedure is terminated. It is contemplated that the electrosurgical procedure may have one or two phases or more than three phases. It is also contemplated that any of the phases may include subphases:

The goal of controlled energy delivery feedback pulsing is to focus power and heat into a localized region and breakdown tissue for division. Methods for achieving the controlled energy delivery include applying energy in three different phases. Phases I, II, III may include various techniques for applying energy to properly divide, according to another embodiment of the present disclosure a related method of energy application is disclosed.

During the first phase, activation occurs which involves the tissue contacting surfaces 36, 38 to come in contact with tissue. The tissue reacts with the tissue contacting surface 36, 38 as energy is applied thereto. During the second phase, after the tissue reacts, the energy is pulsed until a predetermined threshold from about 50Ω to about 2500Ω above the minimum value is reached to create a fine line of desiccation. The pulses may be defined by external variables (e.g., impedance, current, power, voltage, temperature, etc.) which may be monitored by the sensor module 214 during the cutting process or extracted from pre-surgical data. During phase three, a final burst of energy is supplied to the tissue in rapid cycles to divide the tissue.

Figure 5:
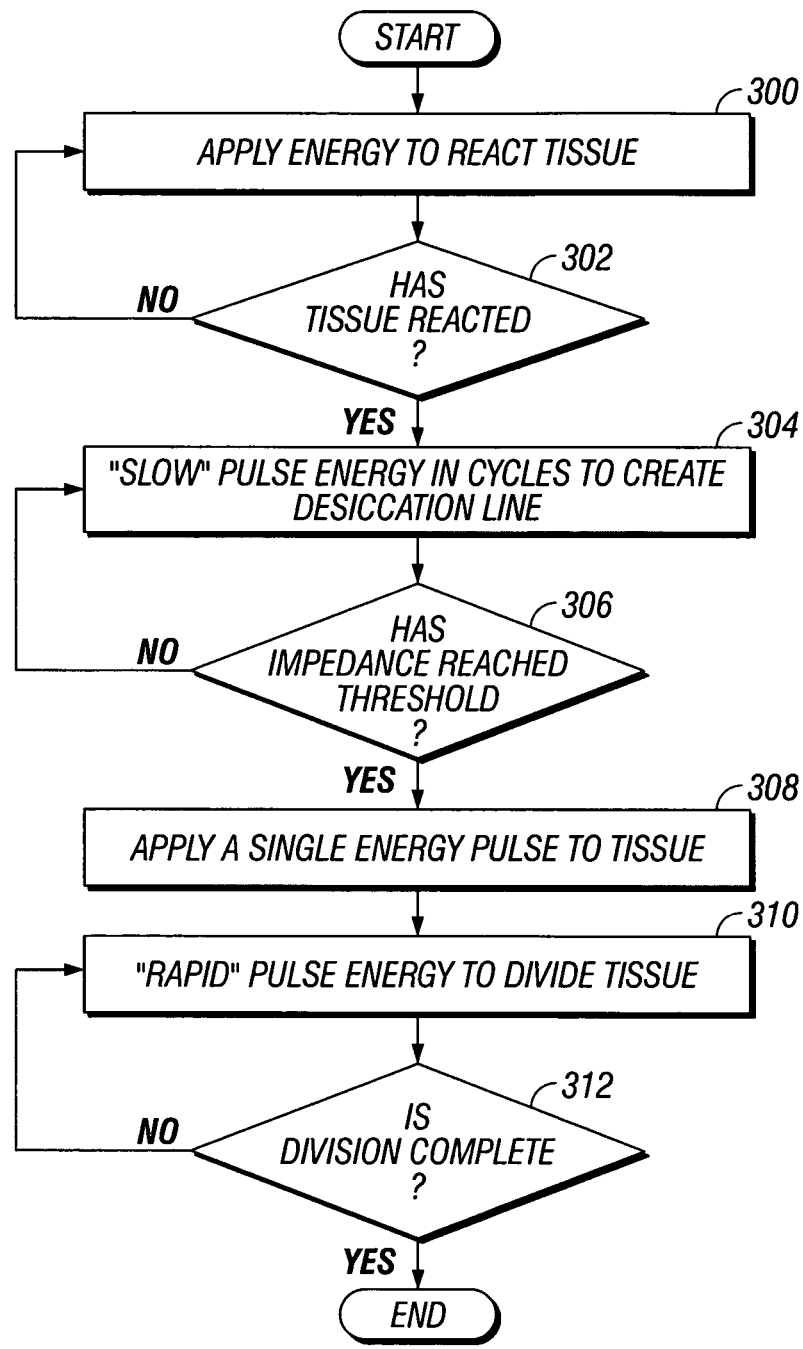
FIG. 5 is a flowchart illustrating a method for regulating application of electrosurgical energy during an electrosurgical procedure in accordance with the present disclosure.
Figure 6:
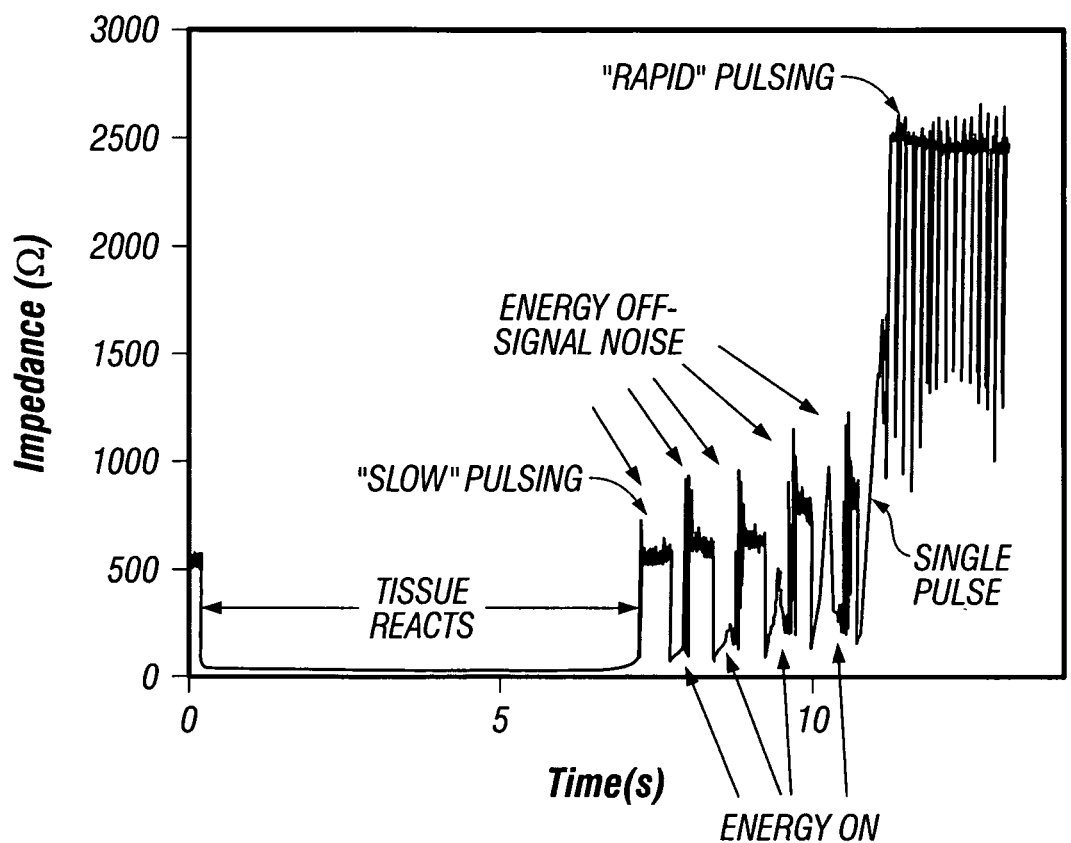
FIG. 6 is a graph of impedance versus time for energy applied during the electrosurgical procedure in accordance with the present disclosure.

The cutting process according to the present disclosure will now be discussed with reference to FIGS. 3 and 4. FIG. 5 shows a flowchart illustrating a method for regulating application of electrosurgical energy and FIG. 6 is a graph of impedance versus time. In step 300 the electrosurgical instrument 12 is placed at a surgical site to divide tissue. Tissue is grasped by the jaw members 30, 32 and the energizable cutting element 40 is brought in contact with the tissue. In addition, energy is supplied to the tissue through the energizable cutting element 40 so that the tissue reacts, which involves preheating the cutting zone.

FIG. 6 shows a graph of impedance over time as tissue is divided according to the method of the present disclosure. Impedance measurement at the tissue may be accomplished by using a sensing current. As the impedance of the tissue changes, the sensing current changes inversely proportionally if the voltage remains constant. This is defined by Ohm's law: V=RI, wherein V is the voltage across the electrodes in volts, I is the current through the electrodes (and tissue) in milliamps and R is the resistance or impedance of the tissue measured in Ohms. By this equation, it can be readily appreciated that when the tissue impedance increases the current will decrease and conversely, if the tissue impedance decreases, the current will increase. Therefore, by measuring the changes in the sensing current the impedance can be measured by the sensor module 214.

In step 302, the control system 18 determines whether the tissue has reacted, as shown in FIG. 6 this occurs from about 50 msec to about 7 sec. Reaction encompasses the vaporization of either or both intra-cellular or extra-cellular fluids and/or the onset of the tissue desiccation process and/or a state change in the tissue that is identifiable by molecular denaturization. The sensor module 214 measures the impedance and transmits the measurement to the control module 204, which compares the measurement to a predetermined threshold (e.g., 1000 Ohms). If the measurement value exceeds the threshold then the control system 18 terminates the energy supply as represented by a flat line in FIG. 6, wherein the line denotes that there was no rise in impedance.

In step 304, a desiccation line is created without completely dividing tissue by "slow" pulsing the energy supplied to the cutting element 40. Pulsing is accomplished by supplying energy in cycles instead of a constant flow. The control system 18 briefly supplies power to the tissue (e.g., 0.5 sec) then terminates the supply for the same period (e.g., 0.5 sec) thereby pulsing the energy. The "slow" pulses are illustrated in FIG. 6 beginning at about 7 seconds and ending at about 10 seconds, where the rise in impedance corresponds to time periods during which energy is supplied and the drop in impedance with energy cut-off. "Slow" pulsing of the energy results in heating and rehydration of the tissue, this gradually breaks down the tissue and produces a fine line of desiccation.

"Slow" pulsing or phase II is accomplished via feedback based pulsing used at this stage in the algorithm. The feedback pulsing is using real-time impedance measurements to determine when to shut the energy off during each pulse. Therefore, each on-pulse duration might be different throughout the stage and is defined by the rate of tissue reaction during the energy delivery and a coded relationship. The on-pulse impedance values that are used to identify the stop point of the on pulse are calculated from the off impedance of the Phase I and an equation built into the logic. The equation can take the form of either a linear or non-linear relationship. Furthermore, the off-times related to these pulses are fixed at 300 ms but it is recognized an operational range exists from 10 ms to 5 seconds. In addition, it is also envisioned that the off-pulses be based on a real-time impedance value as the on pulses with some relationship which is not currently known.

"Slow" pulsing continues until a second threshold is reached. Each pulse raises the impedance of the tissue by a specific amount and, in step 306, after each pulse, the control system 18 determines whether the second impedance threshold has been reached. As illustrated in FIG. 6 that threshold is approximately 1500 Ohms, the threshold for the "slow" pulsing stage can exist from about 50 Ω to about 2500 Ω above the minimum value. If the threshold is not reached, the "slow" pulsing continues, when the threshold has been reached then in step 308, a single energy pulse is applied to the tissue. The single energy pulse is represented in FIG. 6 by an upward sloping line immediately following the "slow" pulsing. In step 310, "rapid" pulsing is commenced to divide the tissue along the desiccation line previously creating during "slow" pulsing. Whereas "slow" pulses apply energy for about 0.5 sec, "rapid" pulses apply energy for about 0.05 sec. The on-times of the rapid pulsing range from about 1 ms to about 1 second and the off-times range from about 1 ms to about 2 second. The "rapid" pulsing continues for approximately 2 seconds until the tissue is divided.

In step 312, the control system 18 determines whether division is complete. This may be accomplished by measuring one or any combination of impedance, phase of the voltage and current, power, and temperature. These measurements are performed by the sensor module 214. Impedance measurement is performed by transmitting a sensing current through the tissue and measuring the impedance thereof. The impedance is then compared by the processor 202, and more specifically by the control module 204, to open circuit impedance of the electrosurgical system 10. If the measured impedance is equal to the open circuit impedance, then division is complete and energy supply is shut off.

Phase detection is accomplished by measuring the phase change between the voltage and current to determine when the separation has occurred. During the division process the voltage and the current are in phase, once the process is complete the voltage and the current are out-of-phase. Thus, detecting when the phase change occurs allows for determining when the division process is complete. The phase measurements are performed by the sensor module 214 and the analysis of the phases of the voltage and current are carried out by the processor 202, and more specifically by the control module 204. Phase encompasses impedance phase as well as the phase angle between current and voltage.

Monitoring power delivery is another way to for determining when the division process has completed. As the division process progresses tissue contact between the cutting element 40 decreases. As a result, power requirements decrease and impedance increases. Once the power level reaches a certain threshold from about 0 W to about 40 W as measured by the sensor module 214, the division process is complete. Comparison and analysis of the power level is carried out by the processor 202, and more specifically by the control module 204.

Monitoring temperature is another method for determining when the division process is complete. The sensor module 214 measures temperature either at the cutting element 40 or the tissue. The temperature is then compared by the processor 202, and more specifically by the control module 204, to determine if it is at or above a predetermined threshold, such as, for example from about 100° C. to about 120° C. If the temperature at the cutting element 40 or the tissue is at or above the threshold then the division process is complete and the energy supply is terminated.

If the division process is not complete (e.g., one of the above measurement are not at or above a predetermined threshold) then the process returns to step 310 where the "rapid" pulsing continues until measurements are taken again to determine if the process is complete.

Those skilled in the art will understand that the impedance values and pulse cycles discussed above are illustrative and that the actual values may vary depending on a plurality of factors (e.g., type of tissue, moisture content, etc.).

Figure 7:
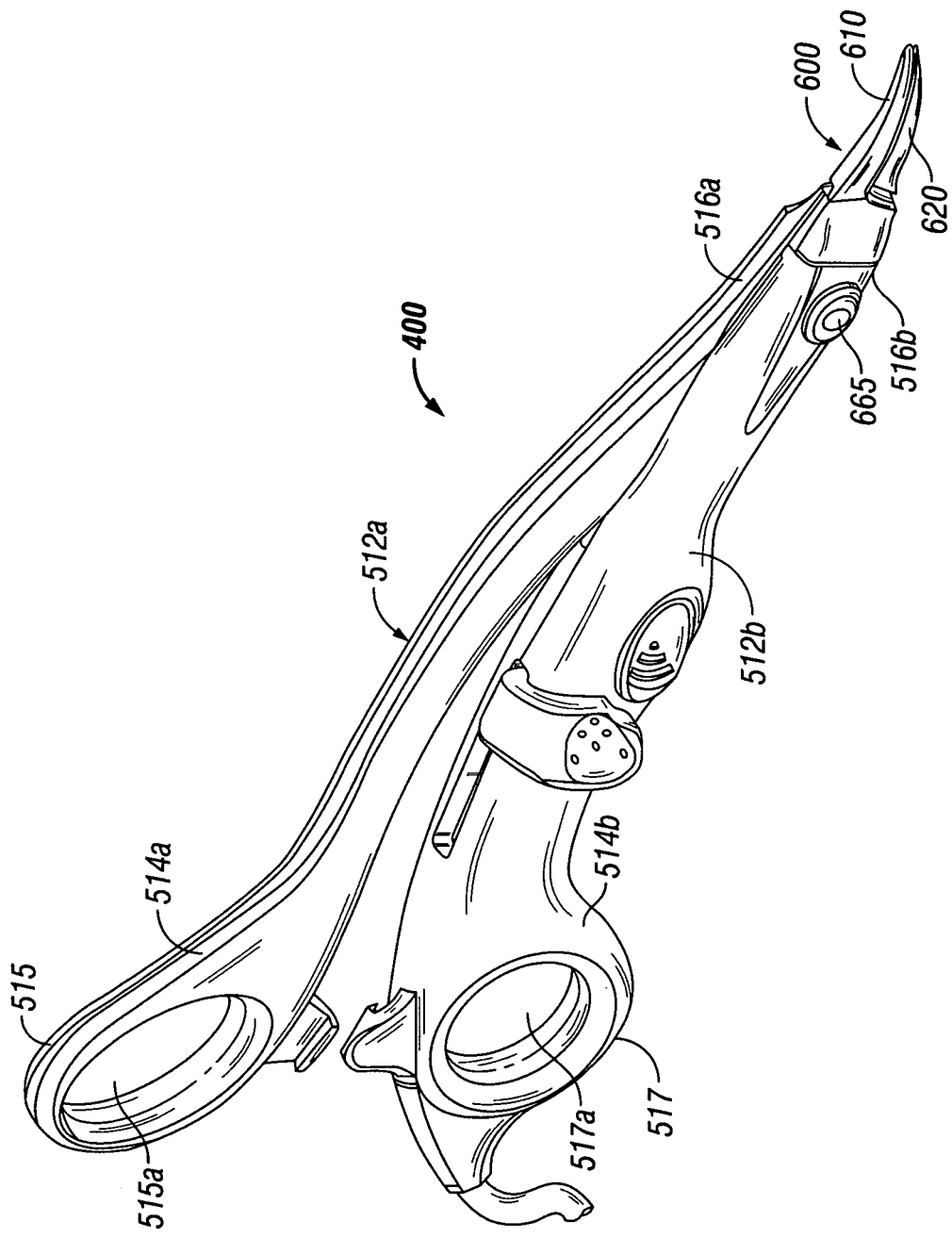
FIG. 7 is a perspective view of an open forceps configured for electrical division of tissue in accordance with the present disclosure.

From the foregoing and with reference to the various figure drawings, those skilled in the art will appreciate that certain modifications can also be made to the present disclosure without departing from the scope of the same. It is envisioned that forceps and/or the electrode assembly of the end effector may be designed such that they are fully or partially disposable or "reposable", i.e., a new or different electrode assembly (or electrode assembly and shaft) selectively replaces the old electrode assembly as needed. Moreover, it is envisioned that a reusable forceps could be sold as a kit having different electrodes assemblies for different tissue types. The surgeon simply selects the appropriate electrode assembly for a particular tissue type. Furthermore, it is contemplated that any pulsing techniques, methods and mechanisms disclosed herein may be employed on a monopolar electrosurgical instrument or open forceps such as the open forceps 400 disclosed in FIG. 7.

The forceps 400 includes an end effector assembly 600 which attaches to the distal ends 516a and 516b of shafts 512a and 512b, respectively. The end effector assembly 600 includes pair of opposing jaw members 610 and 620 which are pivotally connected about a pivot pin 665 and which are movable relative to one another to grasp vessels and/or tissue. An electrically energizable cutting element such as the cutting element 40 described with respect to FIGS. 1-4 may be disposed within the end effector 600. In addition, the generator (not shown) which supplies power to the forceps 400 may be configured to pulse energy to divide tissue in the same manner as discussed above.

Each shaft 512a and 512b includes a handle 515 and 517, respectively, disposed at the proximal end 514a and 514b thereof which each define a finger hole 515a and 517a, respectively, therethrough for receiving a finger of the user. Finger holes 515a and 517a facilitate movement of the shafts 512a and 512b relative to one another which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT", the entire content of which being incorporated by reference herein.

Although the subject electrosurgical generator has been described with respect to preferred embodiments, it will be readily apparent to those having ordinary skill in the art to which it appertains that changes and modifications may be made thereto without departing from the spirit or scope of the subject devices. It is also envisioned that the electrosurgical generator may be controlled to perform any known bipolar or monopolar function such as electrocautery, hemostasis, and/or desiccation utilizing one or both jaw members to treat the tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A system for controlling delivery of energy to divide tissue comprising:
   an electrosurgical instrument having an electrically energizable electrode which communicates energy to the tissue; and
   a generator configured to supply the energy to the electrosurgical instrument which supplies the energy to the tissue in a first phase such that the energy is supplied at a continuous rate to pre-heat or seal the tissue until the tissue reaches a first predetermined threshold, in a second phase such that the energy is supplied at a first rate of pulsing to create a desiccation line until impedance at the tissue has reached a second predetermined threshold, and in a third phase such that the energy is supplied at a second rate of pulsing to divide the tissue across the desiccation line, the second rate of pulsing being greater than the first rate of pulsing, the generator including a sensor configured to monitor impedance of the tissue, wherein the energy is terminated at the first phase, second phase, or third phase when the impedance at the tissue has reached the first predetermined threshold, the second predetermined threshold, or the tissue is substantially divided.

2. A system as in claim 1, wherein the electrosurgical instrument is a bipolar forceps comprising an end effector assembly disposed at a distal end thereof, the end effector assembly including jaw members movable from a first position in spaced relation relative to one another to at least one subsequent position wherein the jaw members cooperate to grasp tissue therebetween, the end effector assembly further includes the electrically energizable electrode.

3. A system as in claim 2, wherein the bipolar forceps is configured for endoscopic surgery.

4. A system as in claim 2, wherein the bipolar forceps is configured for open surgery.

5. A system as in claim 1, wherein the electrosurgical instrument is a monopolar instrument.

6. A system as in claim 1, wherein the second predetermined threshold is from about 50 Ohms to about 2500 Ohms.

7. A system as in claim 1, further comprising:
   a sensor module for measuring at least one of a tissue property and an energy property; and
   a processor for determining when the tissue has been divided as a function of the tissue property.

8. A system as in claim 7, wherein the tissue property is selected from the group consisting of impedance and temperature.

9. A system as in claim 7, wherein the energy property is selected from the group consisting of voltage phase, current phase, and power.

10. A system as in claim 1, wherein the first predetermined threshold is from about 1 Ohms to about 200 Ohms.

\* \* \* \* \*